(12) United States Patent
LeClair

(10) Patent No.: US 7,297,288 B1
(45) Date of Patent: *Nov. 20, 2007

(54) METHOD AND APPARATUS FOR THE CONTROLLED FORMATION OF CAVITATION BUBBLES USING TARGET BUBBLES

(76) Inventor: Mark L. LeClair, 25 Jesse Daniels Dr., Buxton, ME (US) 04093

( * ) Notice: Subject to any disclaimer, the term of this patent is extended or adjusted under 35 U.S.C. 154(b) by 0 days.

This patent is subject to a terminal disclaimer.

(21) Appl. No.: 11/175,878

(22) Filed: Jul. 5, 2005

Related U.S. Application Data

(63) Continuation of application No. 10/263,067, filed on Oct. 1, 2002, now Pat. No. 6,932,914.

(60) Provisional application No. 60/350,849, filed on Jan. 18, 2002.

(51) Int. Cl.
  *B44C 1/22* (2006.01)
(52) U.S. Cl. ............................ 216/83; 216/52; 216/56
(58) Field of Classification Search ................. 216/52, 216/56, 83, 85, 92, 94; 261/194; 606/2, 606/9; 219/121.12
See application file for complete search history.

(56) References Cited

U.S. PATENT DOCUMENTS

| 4,231,657 A | 11/1980 | Iwamatsu |
| 4,759,894 A | 7/1988 | McCorkle |

(Continued)

OTHER PUBLICATIONS

Akhatov et al, Collapse and Rebound of Laser Induced Cavitation Bubble, CAV2001: Fourth International Symposium on Cavitation, California Institute of Technology, Jun. 20-23, 2001.

(Continued)

*Primary Examiner*—A. Farah
(74) *Attorney, Agent, or Firm*—D'Arcy H. Lorimer; Lorimer Labs

(57) ABSTRACT

The present invention discloses a method and apparatus for the directed formation of a re-entrant micro-jet formed upon the collapse of a working cavitation bubble formed proximate to a work surface. A target bubble, formed between the work surface and the working cavitation bubble, is utilized to direct the re-entrant micro-jet to the work surface.

21 Claims, 15 Drawing Sheets

U.S. PATENT DOCUMENTS

| | | | |
|---|---|---|---|
| 5,057,184 A * | 10/1991 | Gupta et al. | 216/65 |
| 5,437,729 A | 8/1995 | Boatner et al. | |
| 6,139,543 A * | 10/2000 | Esch et al. | 606/7 |
| 6,932,914 B2 * | 8/2005 | LeClair | 216/52 |
| 6,960,307 B2 * | 11/2005 | LeClair | 216/52 |
| 2002/0034610 A1 | 3/2002 | Perez et al. | |
| 2002/0045977 A1 | 4/2002 | Fletcher et al. | |
| 2004/0004055 A1 * | 1/2004 | Barros | 216/13 |
| 2004/0054357 A1 * | 3/2004 | O'Donnell | 606/4 |
| 2005/0064137 A1 * | 3/2005 | Hunt et al. | 428/131 |

OTHER PUBLICATIONS

Ishida et al, Cavitation Bubble Behavior Near Solid Boundaries, CAV2001: Fourth International Symposium on Cavitation, California Institute of Technology, Jun. 20-23, 2001.

Blake et al, Boundary Integral Methods for Cavitation Bubbles Near Boundaries, CAV2001: Fourth International Symposium on Cavitation, California Institute of Technology, Jun. 20-23, 2001.

Baghdassarain et al, Spectrum of Luminescence from Laser Induced Bubbles in Water and Cryogenic Fluids, CAV2001: Fourth International Symposium on Cavitation, California Institute of Technology, Jun. 20-23, 2001.

Tomita et al, Energy Evaluation of Schock Wave Emission and Bubble Generation by Laser Focussing in Liquid Nitrogen, CAV2001:Fourth International Symposium on Cavitation, California Institute of Technology, Jun. 20-23, 2001.

Christopher E. Brennen, Cavitation ad Bubble Dynamics, Oxford U. Press, NY NY, 1995, pp. 70-76.

* cited by examiner

Section B-B from Figure 11

METHOD AND APPARATUS FOR THE CONTROLLED FORMATION OF CAVITATION BUBBLES USING TARGET BUBBLES

CROSS REFERENCE TO RELATED APPLICATIONS

This application is a continuation application of co-pending non-provisional application Ser. No. 10/263,067 filed Oct. 1, 2002 entitled METHOD AND APPARATUS FOR THE CONTROLLED FORMATION OF CAVITATION BUBBLES USING TARGET BUBBLES, now U.S. Pat. No. 6,932,914, which claims the benefit of provisional application No. 60/350,849 filed Jan. 18, 2002 entitled METHOD AND APPARATUS FOR THE CONTROLLED FORMATION OF CAVITATION BUBBLES, and claims benefit thereof. The aforementioned applications are herein incorporated by reference in their entirety.

BACKGROUND OF THE INVENTION

1. Field of the Invention

This invention relates generally to the formation and control of individual micron size and submicron size cavitation bubbles for use in nanofabrication operations. More particularly, embodiments of the invention teach methods and apparatus for control of a re-entrant micro-jet formed upon collapse of an individual or array of cavitation bubbles and directing the impact of the micro-jet toward a work surface or other objects with a high degree of precision.

2. Description of the Related Art

In general, the production of cavitation has been a phenomena many have tried to avoid. Cavitation in a liquid is the formation, growth, and collapse of gaseous and vapor bubbles due to the reduction of pressure below the vapor pressure of the liquid at the working temperature. Pump impellers, boat props, and similar applications experience cavitation which can produce rapid damage and erosion of surfaces. It has been well known for many years that ultrasonic cleaning devices, which function by the creation of cavitation bubbles, can produce significant surface damage to even the hardest of materials. Studies by a number of authors have revealed that one significant element in producing the damage caused by cavitation occurs when a cavitation bubble collapses in the vicinity of a surface, launching what is called a re-entrant micro-jet toward the surface. This liquid jet can produce velocities as high as 1500 m/s, and is capable of damaging the hardest materials known.

Recently, a number of applications have been developed utilizing the formation of cavitation bubbles through the use of laser light or electrical discharge. Esch et al. (U.S. Pat. No. 6,139,543) and Herbert et al. (U.S. Pat. No. 6,210,400) disclose the use of laser light introduced into a catheter device for the purpose of creating cavitation bubbles, whose expansion and collapse are utilized to pump fluids in and out of the catheter. Hammer et al. (U.S. Pat. No. 5,738,676) discloses a laser surgical probe with a special lens designed to produce the cavitation bubbles further from the end of the fiber optics, to reduce the damage formed (presumably by the re-entrant micro-jets launching into the lens on the end of the cable). Such damage was also reported by Rol et al. in "Q Switched Pulses and Optical Breakdown Generation Through Optical Fibers", *Laser and Light in Opthalmology*, Vol. 3, No. 3, 1990. Palanker (U.S. Pat. No. 6,135,998) describes a method for performing electrosurgery using sub-microsecond, high power electrical pulses are applied to an electrosurgical probe interface. The tool described by Palanker provides a cutting force by both the plasma generated by the electrical arc and shock waves produced by collapsing cavitation bubbles.

In each of the prior art references cited above, there has been no attempt to control the direction and impact of the powerful micro-jets formed upon the collapse of the cavitation bubbles created when highly focused energy is introduced into a liquid. Without such control, concern of collateral damage cannot be avoided, especially when such tools are used in the human body in a medical application.

Recently as well, there has been a significant interest generated in the field of nanotechnology, for methods needed to fabricate micron and submicron devices and nanomachines. There are very few fabrication tools available that can cut, drill, peen, deform, or otherwise modify features of a surface on a submicron to nanometer scale. Much of the technology developed by the semiconductor industry requires the fabrication of structures utilizing photolithographic processing. This technology is not as flexible as may be required, and will have certain difficulties when applied to biological nanotechnology systems. Advancing the state of the art required by nanotechnology applications will require fabrication technologies operating at least 1 to 2 orders of magnitude below that capable in the semiconductor process arena.

The invention as described in the above referenced provisional application provides a method for the controlled formation of individual cavitation bubbles comprising immersing a mask including at least one aperture within a liquid, immersing a work piece having a work surface in the liquid proximate to the mask, generating a cavitation bubble proximate to the aperture such that the mask is located between the cavitation bubble and the work piece. A re-entrant micro-jet formed during the collapse of the cavitation bubble is directed through the aperture to the work surface. An apparatus for the controlled formation of cavitation bubbles as described in the above referenced provisional application discloses a mask having at least one aperture, immersed in a liquid, and an energy source having an energy flow in the liquid sufficient to create at least one cavitation bubble. The energy flow creates the cavitation bubble proximate to the aperture and the collapse of the cavitation bubble creates a re-entrant micro-jet directed through the aperture to a work surface. While this technique is very useful for processing surfaces that can be located conveniently in the vicinity of a fixed orifice, there are many other situations where one may wish dynamic, three dimensional control of the direction of the re-entrant micro-jet. These situations may include eye surgery, for example, where placing an orifice structure inside the eye may not be practical.

The prior state of the art therefore has yet to provide a fabrication technology capable of operating in the nanometer region by harnessing the powerful phenomena of the re-entrant micro-jet formed during the collapse of a precisely located cavitation bubble. What is further needed is a method and apparatus to precisely control the direction and location of the re-entrant micro jet without the encumbrance of physical structure such an orifice between the work surface and the cavitation bubble.

SUMMARY OF THE INVENTION

The present invention provides a method for the directed formation of a re-entrant micro-jet including generating a working cavitation bubble proximate to a work surface and generating a target bubble between the work surface and the working cavitation bubble, wherein a re-entrant micro-jet formed upon the collapse of the working cavitation bubble is directed to the work surface.

An apparatus for the directed formation of a re-entrant micro-jet in accordance with the present invention includes a first energy source having an energy flow in the liquid sufficient to create a working cavitation bubble proximate to a work surface and a second energy source having a second energy flow in the liquid sufficient to create a target cavitation bubble between the work surface and the working cavitation bubble. The re-entrant micro-jet formed upon the collapse of the working cavitation bubble is directed to the work surface.

DETAILED DESCRIPTION OF THE PREFERRED EMBODIMENT(S)

The control and direction of the re-entrant micro-jet formed during the collapse of a cavitation bubble can provide a powerful tool for performing various fabrication and manipulation functions at a submicron and nanometer scale. A previous application (60/350,849 filed Jan. 18, 2002 entitled METHOD AND APPARATUS FOR THE CONTROLLED FORMATION OF CAVITATION BUBBLES) describes how these re-entrant micro-jets may be controlled through the use of an orifice placed between the work surface and the collapsing cavitation bubble. While the aforementioned techniques shall prove very useful for fabrication processes where the work surface can be placed in proximity to an orifice structure, there may be other applications where placing such a structure will be difficult or impossible. One example might be surgery inside the human eye, where a surgeon might wish to generate re-entrant micro-jets in the humus by focussing laser beams through the cornea. Another example might be to cut features into the side wall of micron sized pores in an integrated circuit structure where fabricating and placing submicron orifice structures would be very difficult.

The present invention teaches a technique by which the re-entrant micro-jet formed during the collapse of a cavitation bubble (working bubble) can be directed by the creation of a target bubble within a given proximity of the collapsing working bubble. Target bubbles can be created in any direction in 3d space relative to the center of the working bubble. All that is required is that there be a clear line of sight (relative to the radiation source needed to create the bubble) to the projected position of the target bubble, that the target bubble is formed within a given time period of the collapse of the working bubble, and that the target bubble be within a given proximity of the working bubble. The target bubble serves to attract the re-entrant micro-jet by creating a hydrodynamic condition similar to that of a solid work surface or an orifice. However, the target bubbles, unlike solid work surfaces, are transparent to the jets, and allow the jets to slice through them unimpeded. Target bubbles can therefore be used to direct the powerful re-entrant micro-jets toward a work surface or object without the need for an orifice. To be effective, a target bubble should be within approximately 6 working bubble diameters of the working bubble. A working bubble diameter is defined as the maximum diameter obtained by the working bubble just prior to collapse.

Figure 1:
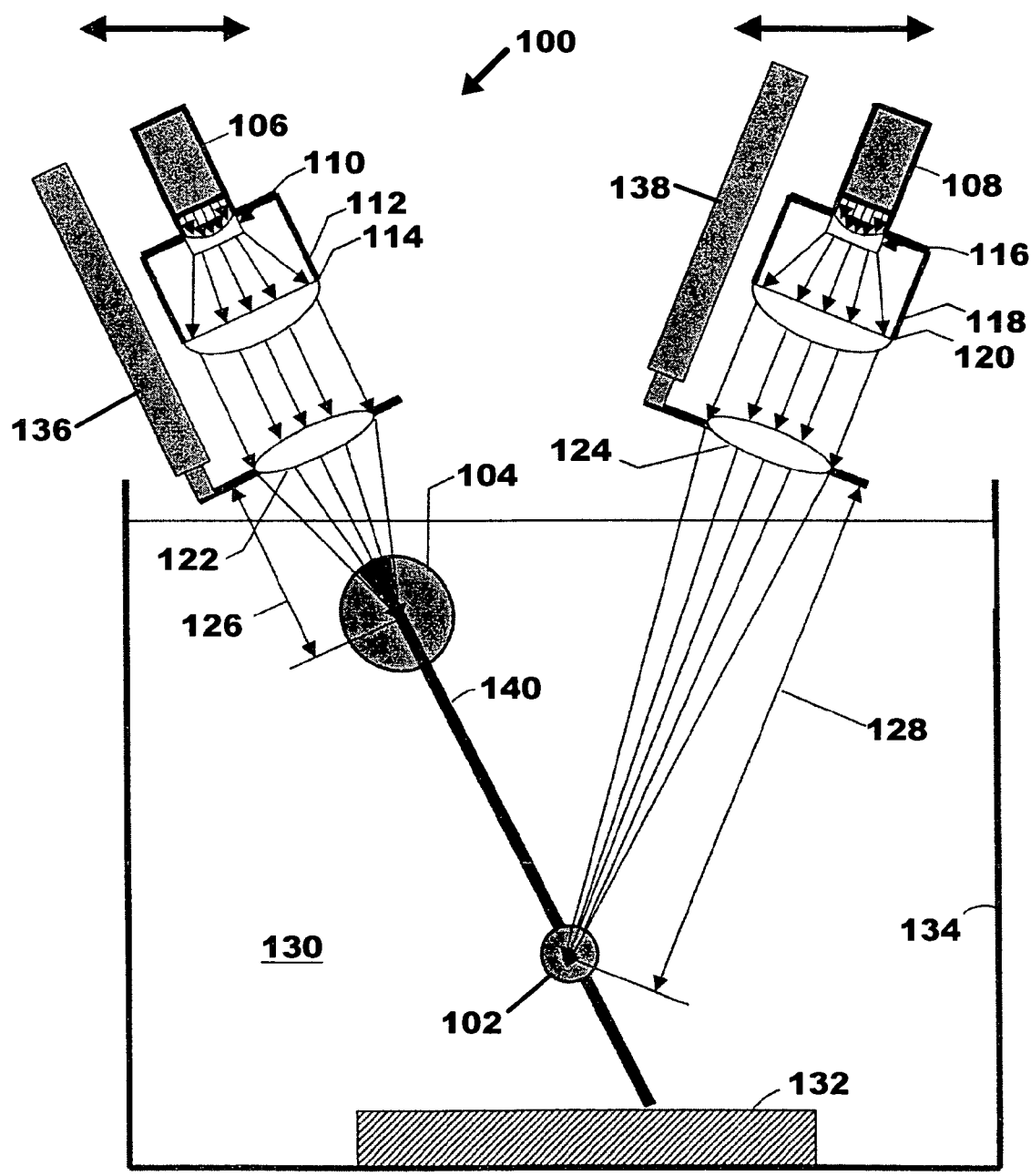
FIG. 1 is a cross sectional view of an apparatus for generating target bubbles and cavitation bubbles in accordance with one embodiment of the present invention.

FIG. 1 is a cross sectional view of an apparatus 100 for generating target bubbles 102 and cavitation bubbles 104 in accordance with one embodiment of the present invention. A work piece 132 is placed in a container 134 filled with fluid 130. Components 108, 116, 118, 120, 124, and 138 make up the focussed laser device for creating the target bubble 102. Components 106, 110, 112, 114, 122, and 136 make up the focussed laser device for creating the cavitation working bubble 104. The lasers 106 and 108 may be chosen from among the group of $CO_2$, Nd-YAG, dye, or excimer types. Other focussed energy devices such as x-ray and electrical discharge electrodes may also be used to create bubbles 104 and 106, as is well known to those skilled in the art. Alternatively, target bubbles 102 may be created by sparging gas though nozzles and orifices, and allowing them to rise through the fluid proximate to the working bubble. Radiation produced by laser 108 is collimated by lens components 116 and 120 and focussed distance 128 by lens 124. The intense laser radiation focussed into a small control volume vaporizes the liquid in that volume and creates the cavitation target bubble 102. In like manner, laser 106 and lens components 110, 114, and 122 create the cavitation working bubble 104 at a distance 126. Re-entrant micro-jet 140 is formed upon the collapse of the working cavitation bubble 104, and is attracted through target bubble 102 to work surface 132. By altering the angular orientation of lasers 106 and 108, and the focal distances 126 and 128, the re-entrant micro-jet can be positioned to impact anywhere on work surface 132. By altering the distance of the working bubble 104 to the work surface 132, the impact force of the jet may also be altered. To be effective in directing the re-entrant micro-jet, the target bubble should be approximately within six (maximum) working bubble diameters of the working bubble. The fluid in tank 134 can be any fluid that absorbs the laser radiation being utilized, but is preferably water or solutions containing water. The fluid may be re-circulated and filtered by additional pumps and components (not shown) to maintain an appropriate optical clarity.

Figure 2:
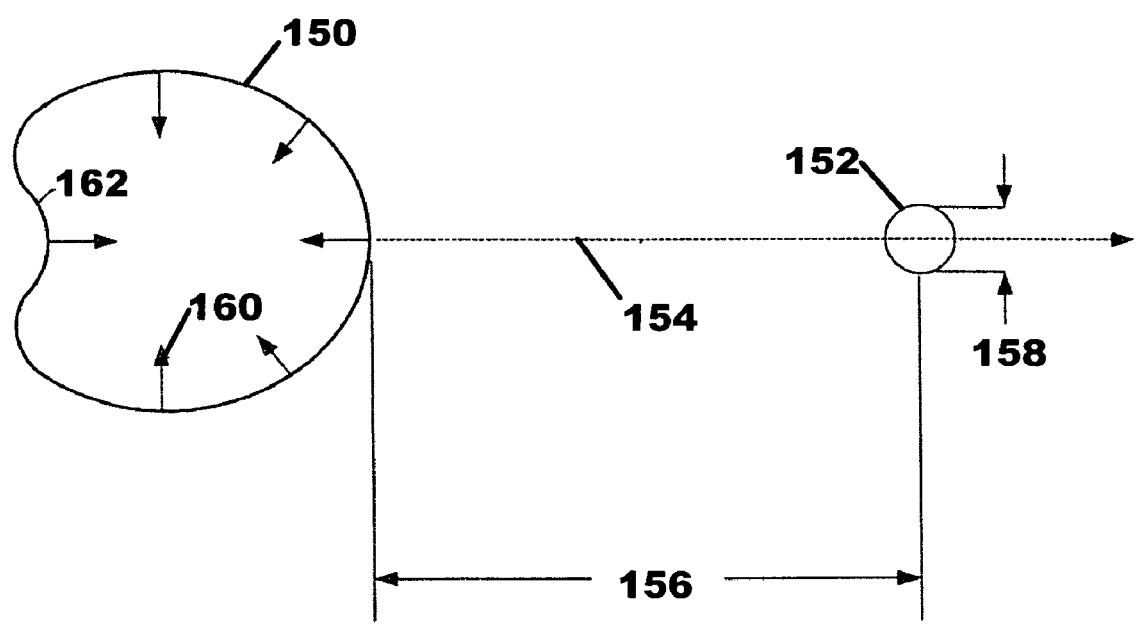
FIG. 2 is a schematic view of a collapsing, working cavitation bubble in relationship to a target bubble in accordance with one embodiment of the present invention.

FIG. 2 is a schematic view of a collapsing, working cavitation bubble 150 in relationship to a target bubble 152 in accordance with one embodiment of the present invention. As previously stated, distance 156 should be approximately less than six maximum working bubble diameters. To attract the re-entrant micro-jet formed as bubble 150 collapses, target bubble diameter 158 should be greater than approximately 10% of the maximum working bubble diameter. The projected path of the re-entrant micro-jet is shown by dashed line 154. Inwardly directed arrows 160 in bubble 150 illustrate the beginning collapse of the outer bubble surface. Concave surface 162 is indicative of the direction toward which the jet will be launched. Target bubble 152 may also be a cavitation bubble in an expanding or contracting state, as long as its diameter meets the minimum criteria stated above as working bubble 150 begins to collapse.

FIGS. 3a-3e are schematic diagrams showing a sequence for directing a re-entrant micro-jet toward a work surface through a target bubble in close proximity to the working bubble in accordance with one embodiment of the present invention.

Figure 3A:
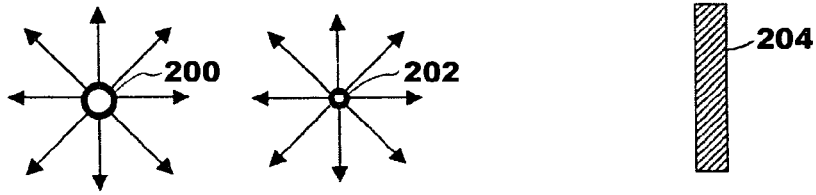
FIGS. 3a-3e are schematic diagrams showing a sequence for directing a re-entrant micro-jet toward a work surface through a target bubble in close proximity to the working bubble in accordance with one embodiment of the present invention.

FIG. 3a shows a target cavitation bubble 202 formed in close proximity to a working cavitation bubble 200. Both bubbles are initiated at approximately the same time, the arrows emanating from the surface pointing outward illustrate an expanding condition for each bubble. The target bubble 202 is placed between the working bubble 200 and the work piece 204. In this example; the target bubble 202 is within six working bubble diameters of the working bubble 200, and is also within six target bubble diameters of the working bubble 200. The working bubble 200 is greater than six working bubble diameters from the work piece 204. As illustrated, the target bubble 202 is smaller in diameter than the working bubble 200.

Figure 3B:
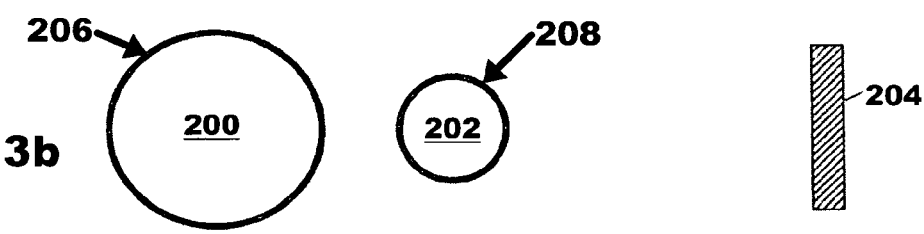

FIG. 3b shows the working bubble 206 and target bubble 208 at their maximum expanded diameters, just before they collapse.

Figure 3C:
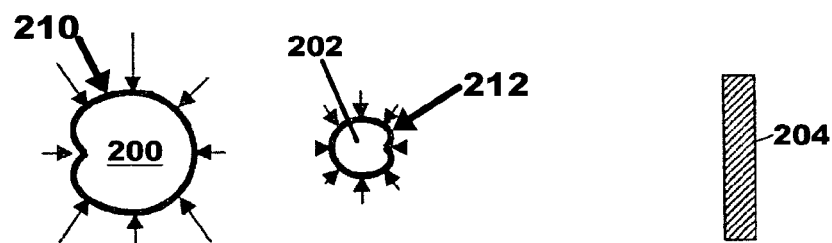

FIG. 3c shows both bubbles 210 and 212 beginning to collapse, as illustrated by the inwardly directed arrows on their outer surface.

Figure 3D:
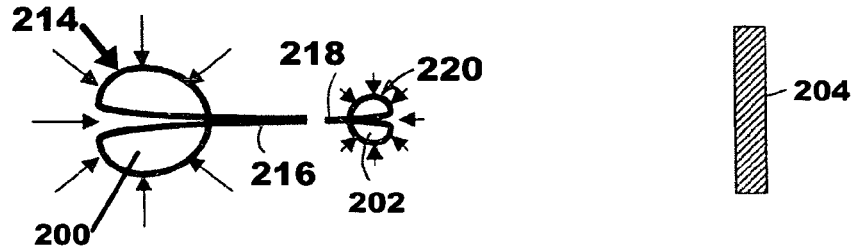

FIG. 3d shows the initial formation of the re-entrant micro-jets 216 and 218 by each of the bubbles 214 and 220, respectively. Due to their close proximity, opposing jets are launched from each bubble toward each other.

Figure 3E:
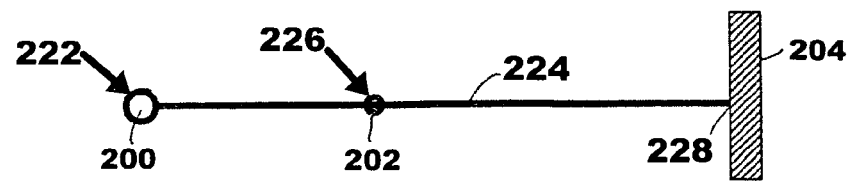

FIG. 3e shows the net effect of the re-entrant micro-jet 224 launched through the target bubble 220, 226 to the work surface 228. Since the working bubble 222 was initiated as a larger bubble in comparison to the target bubble, the re-entrant micro-jet launched from it (222) is dominant, resulting in a jet directed toward the work surface. However, the impact force imparted by jet 224 is reduced by the opposing interaction of jet 218 (launched from the target bubble 220, 226) on the initial jet 216. This phenomena may be utilized to moderate and control the impact force imparted by jet 224 on the work surface 204. The closer bubbles 206 and 208 are in maximum diameter, the lower the net force delivered to the work piece 204.

FIGS. 4a-4e are schematic diagrams showing a sequence for directing a re-entrant micro-jet toward a work surface through a target bubble far from the working bubble in accordance with one embodiment of the present invention.

Figure 4A:
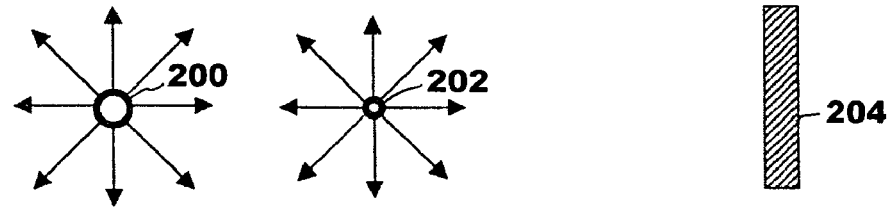
FIGS. 4a-4e are schematic diagrams showing a sequence for directing a re-entrant micro-jet toward a work surface through a target bubble far from the working bubble in accordance with one embodiment of the present invention.

FIG. 4a shows a target cavitation bubble 202 formed in moderate proximity to a working cavitation bubble 200. Both bubbles are initiated at approximately the same time, the arrows emanating from the surface pointing outward illustrate an expanding condition for each bubble. The target bubble 202 is placed between the working bubble 200 and the work piece 204. The working bubble 200 is greater than six working bubble diameters from the work piece 204. In this example, the target bubble 202 is within six working bubble diameters of the working bubble 200, but is greater than six target bubble diameters from the working bubble 200. As illustrated, the target bubble 202 is smaller in diameter than the working bubble 200.

Figure 4B:
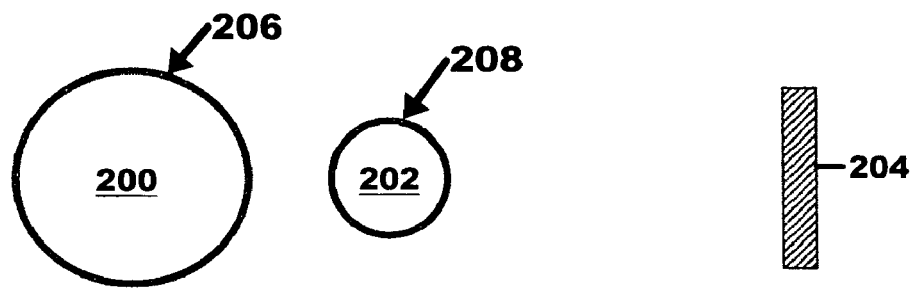

FIG. 4b shows the working bubble 206 and target bubble 208 at their maximum expanded diameters, just before they collapse.

Figure 4C:
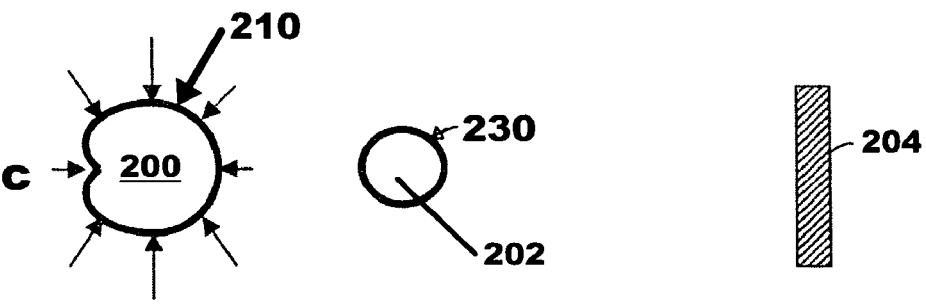

FIG. 4c shows both bubbles 210 and 230 beginning to collapse, as illustrated by the inwardly directed arrows on their outer surface.

Figure 4D:
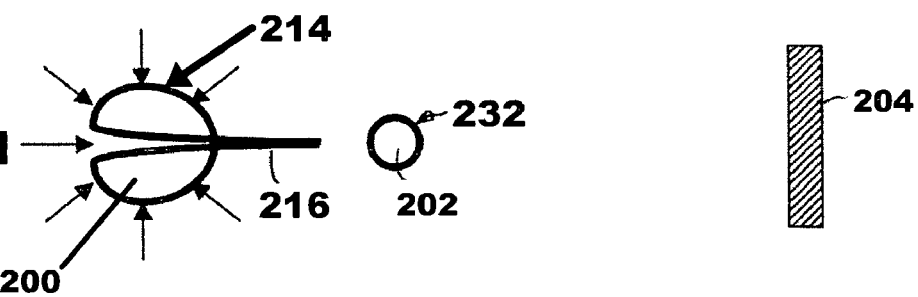

FIG. 4d shows the initial formation of the re-entrant micro-jet 216 by bubble 214. Since target bubble 232 is further than six target bubble diameters from bubble 214, it does not "sense" (fluid mechanically) the presence of working bubble 214 and therefore will not launch a jet in its direction. However, target bubble 230 is within six working bubble diameters of bubble 214, attracting the re-entrant micro-jet from collapsing working bubble 214.

Figure 4E:
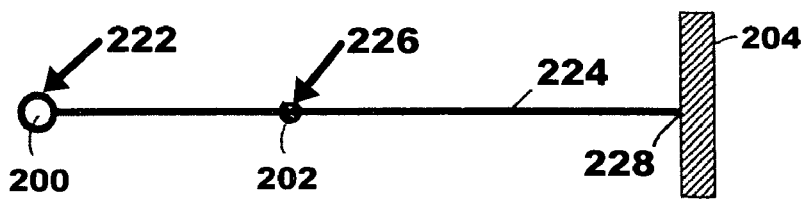

FIG. 4e shows the net effect of the re-entrant micro-jet 224 launched through the target bubble 226 to the work surface 228. The full force of the re-entrant micro-jet formed upon the collapse of the working cavitation bubble is applied to the work surface 228.

FIGS. 5a-5e are schematic diagrams showing a sequence for directing a re-entrant micro-jet toward a work surface at an angle in accordance with one embodiment of the present invention.

Figure 5A:
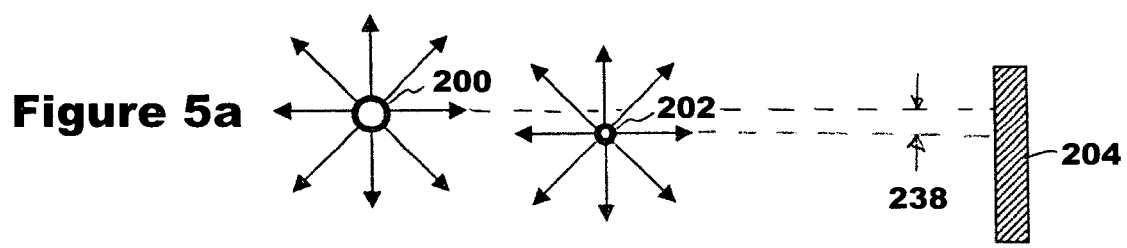
FIGS. 5a-5e are schematic diagrams showing a sequence for directing a re-entrant micro-jet toward a work surface at an angle in accordance with one embodiment of the present invention.

FIG. 5a shows a target cavitation bubble 202 formed in moderate proximity to a working cavitation bubble 200. Both bubbles are initiated at approximately the same time, the arrows emanating from the surface pointing outward illustrate an expanding condition for each bubble. The target bubble 202 is placed between the working bubble 200 and the work piece 204, situated to direct the re-entrant micro-jet from the working bubble 200 at an angle to the surface of 204. The working bubble 200 is greater than six working bubble diameters from the work piece 204. In this example, the target bubble 202 is within six working bubble diameters of the working bubble 200, but is greater than six target bubble diameters from the working bubble 200. As illustrated, the target bubble 202 is smaller in diameter than the working bubble 200.

Figure 5B:
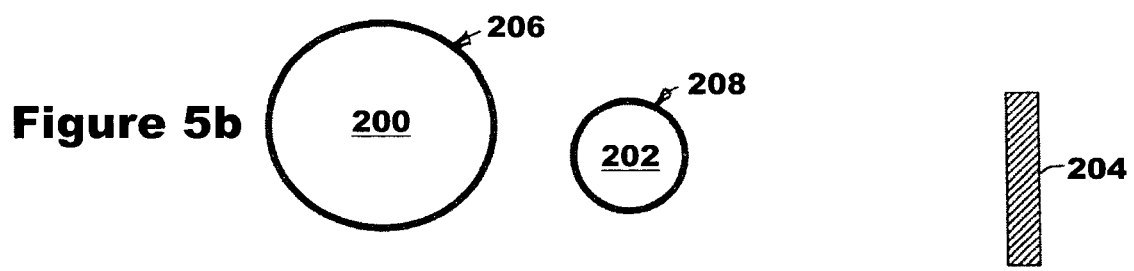

FIG. 5b shows the working bubble 206 and target bubble 208 at their maximum expanded diameters, just before they collapse.

Figure 5C:
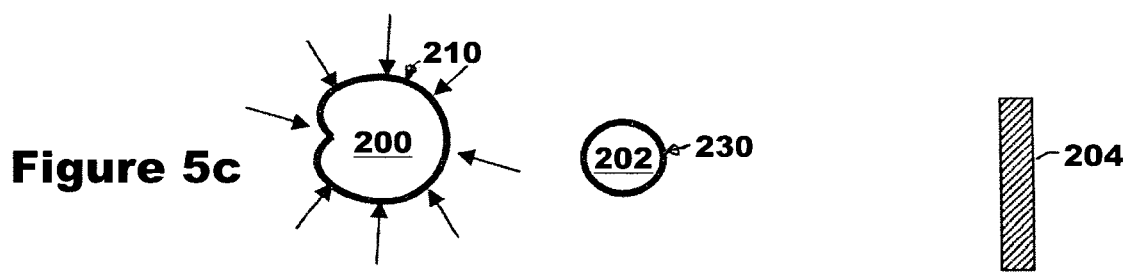

FIG. 5c shows both bubbles 210 and 230 beginning to collapse.

Figure 5D:
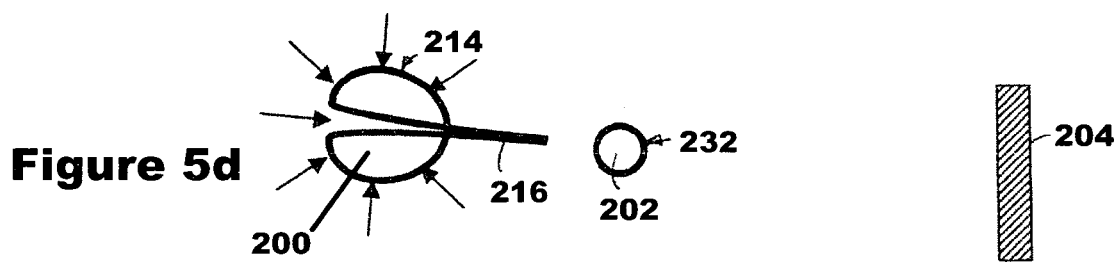

FIG. 5d shows the initial formation of the re-entrant micro-jet 216 by bubble 214. Since target bubble 232 is further than six target bubble diameters from bubble 214, it does not "sense" (fluid mechanically) the presence of working bubble 214 and therefore will not launch a jet in its direction. Target bubble 230 is within six working bubble diameters of bubble 214, attracting the re-entrant micro-jet from collapsing working bubble 214.

Figure 5E:
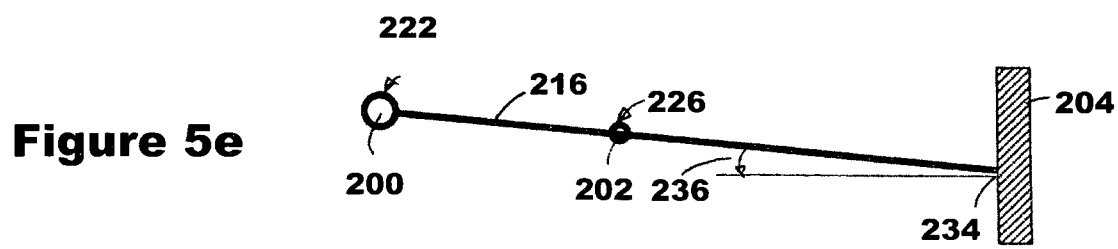

FIG. 5e shows the net effect of the re-entrant micro-jet 224 launched through the target bubble 226 to the work surface 234. The full force of the re-entrant micro-jet formed upon the collapse of the working cavitation bubble is applied to the work surface 234, at an angle 236. In this manner the target bubble may be used to direct the jet in any suitable angle with the work surface.

FIGS. 6a-6e are schematic diagrams showing a sequence for directing a re-entrant micro-jet toward a work surface at an angle, for working bubbles and target bubbles in close proximity to the working surface in accordance with one embodiment of the present invention.

Figure 6A:
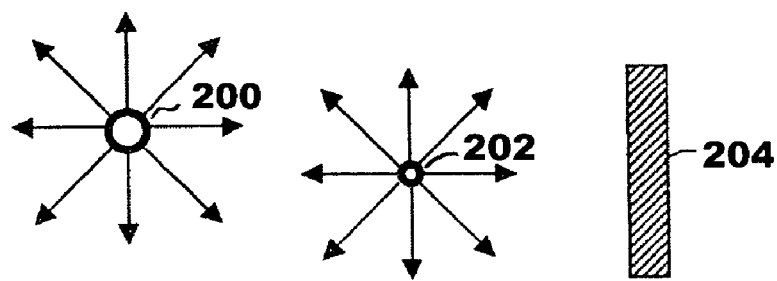
FIGS. 6a-6e are schematic diagrams showing a sequence for directing a re-entrant micro-jet toward a work surface at an angle, for working bubbles and target bubbles in close proximity to the working surface in accordance with one embodiment of the present invention.

FIG. 6a shows a target cavitation bubble 202 formed in moderate proximity to a working cavitation bubble 200. Both bubbles are initiated at approximately the same time, the arrows emanating from the surface pointing outward illustrate an expanding condition for each bubble. The target bubble 202 is placed between the working bubble 200 and the work piece 204, situated to direct the re-entrant micro-jet from the working bubble 200 at an angle to the surface of 204. The working bubble 200 is less than six working bubble diameters from the work piece 204. In this example, the target bubble 202 is within six working bubble diameters of the working bubble 200, but is greater than six target bubble diameters from the working bubble 200. As illustrated, the target bubble 202 is smaller in diameter than the working bubble 200.

Figure 6B:
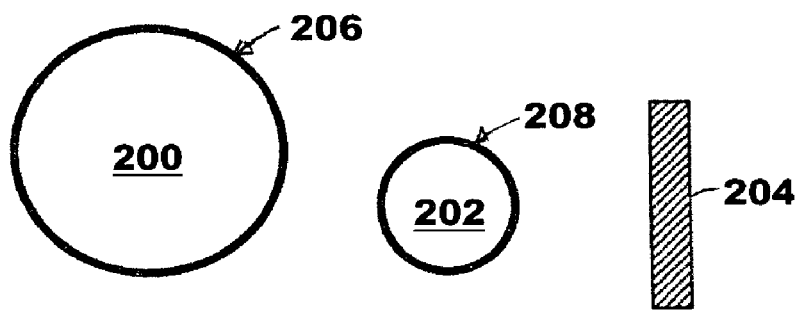

FIG. 6b shows the working bubble 206 and target bubble 208 at their maximum expanded diameters, just before they collapse.

Figure 6C:
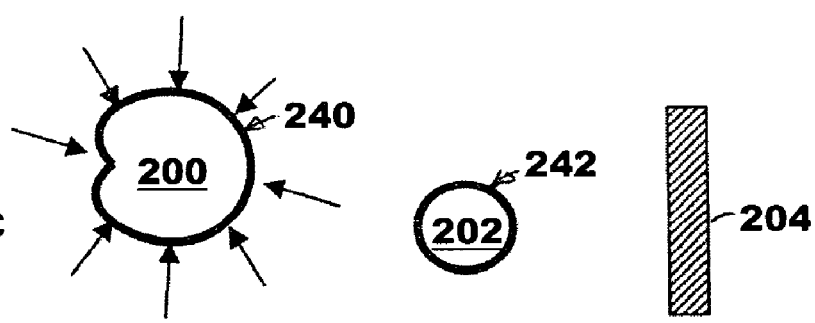

FIG. 6c shows both bubbles 240 and 242 beginning to collapse.

Figure 6D:
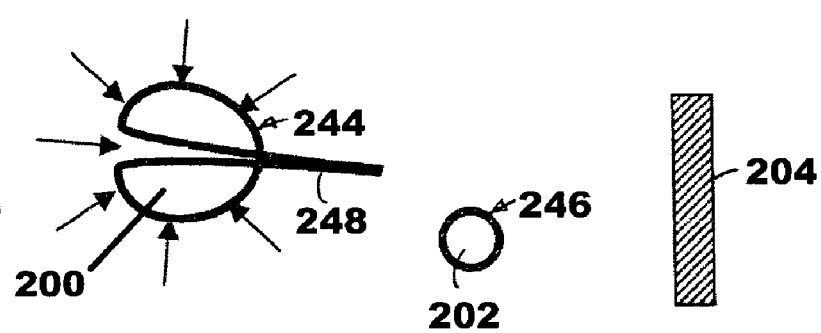

FIG. 6d shows the initial formation of the re-entrant micro-jet 248 by bubble 244. Since target bubble 246 is further than six target bubble diameters from bubble 244, it does not "sense" (fluid mechanically) the presence of working bubble 244 and therefore will not launch a jet in its direction. Since both the target bubble 246 and the working bubble 244 are within six working bubble diameters of the surface of work piece 204, the re-entrant micro-jet from collapsing working bubble 244 is launched in a direction between a path normal to the work surface and a path through target bubble 246. In the absence of any target bubble, the re-entrant micro-jet would be launched in a direction normal to the surface, but the location of impact would be unpredictable.

Figure 6E:
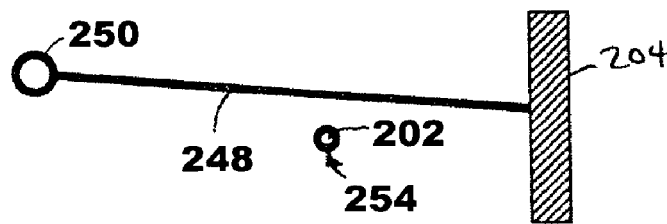

FIG. 6e shows the net effect of the re-entrant micro-jet 252 launched near the target bubble 254 (but not through it) to the work piece 204.

Figure 7:
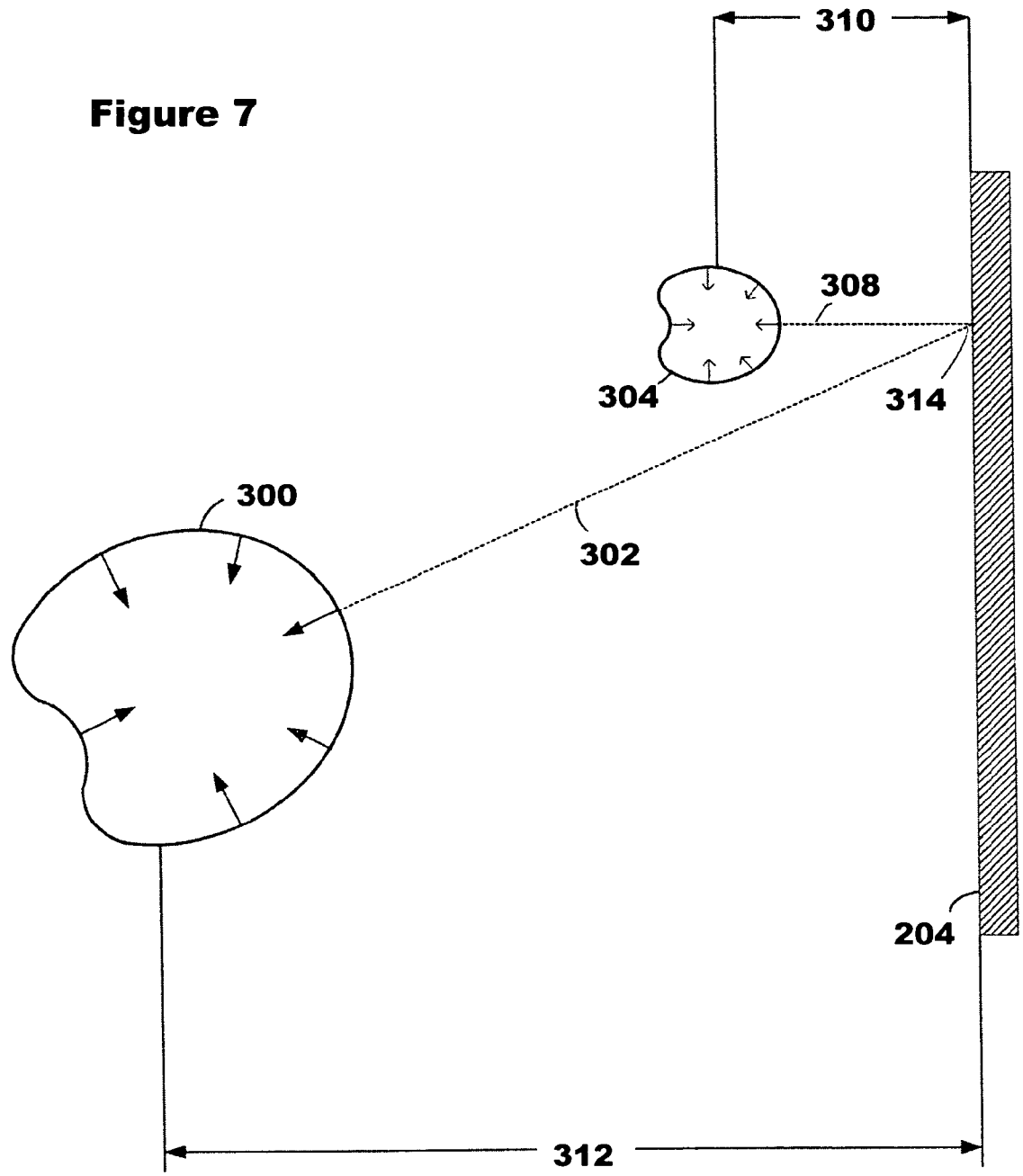
FIG. 7 is a schematic diagram of a working bubble and a target bubble directing convergent re-entrant micro-jets to a work surface in accordance with one embodiment of the present invention.

FIG. 7 is a schematic diagram of a working bubble 300 and a target bubble 304 directing convergent re-entrant micro-jets 302, 308 to a work surface 314 in accordance with one embodiment of the present invention. In this case, distance 312 is less than six working bubble diameters and distance 310 is less than six target bubble diameters. For target bubbles 304 significantly smaller than working bubbles 300, the re-entrant micro-jets emanating from the target bubble will be directed toward the surface 314. It is possible to adjust the spatial position of working bubble 300 in order to direct its re-entrant micro-jet 302 to a position convergent with jet 308 from the target bubble 304, as was shown in FIGS. 6a-e. This technique may be useful for amplifying the impact of the jets upon the work surface, or providing-jets from two different angles to the same location.

Figure 8:
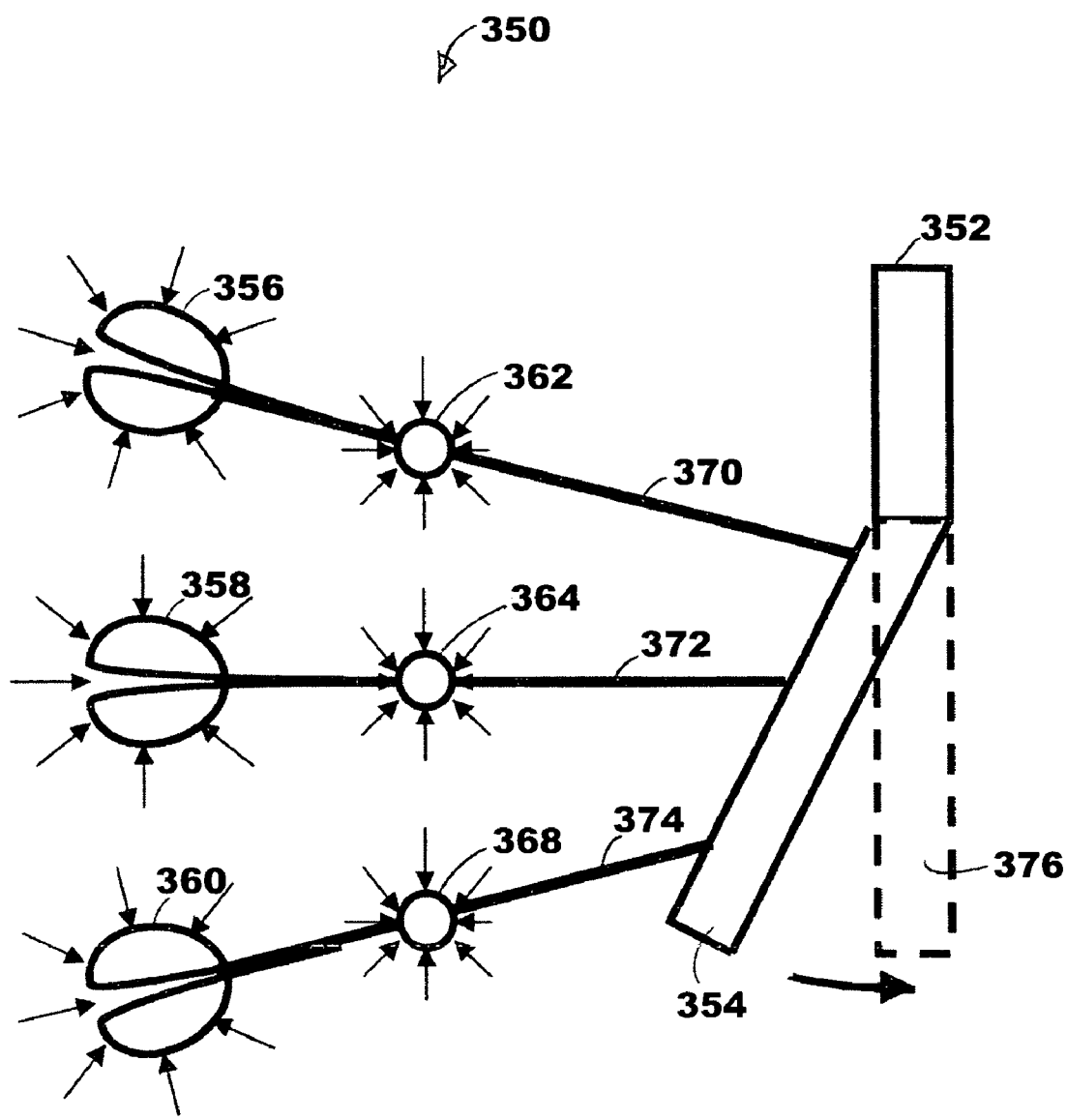
FIG. 8 is a schematic diagram of three re-entrant micro-jets being directed at a movable work piece in accordance with one embodiment of the present invention.

FIG. 8 is a schematic diagram 350 of three re-entrant micro-jets being directed at a movable work piece in accordance with one embodiment of the present invention. Three re-entrant micro-jets 370, 372, and 374 are directed at a movable section 354 of work piece 352. Jet 370 is formed by the collapse of cavitation bubble 356 through target bubble 362. Jet 372 is formed by the collapse of cavitation bubble 358 through target bubble 364. Jet 374 is formed by the collapse of cavitation bubble 360 through target bubble 368. Cavitation bubbles 356, 358, and 360 may be formed simultaneously or in a sequence, depending on the sequence of forces required to locate movable member 354 to its desired location 376. This process may be applied, for example, by a surgeon who wants to precisely locate a small section of tissue that has become detached from its desired position. A folded retina is one such possibility. By adjusting the distance of bubbles 356, 358, and 360 to work piece 354, and their maximum diameters, the forces imparted to tissue may be carefully adjusted to a level sufficient to do the job without imparting collateral damage to the structures being moved.

Figure 9:
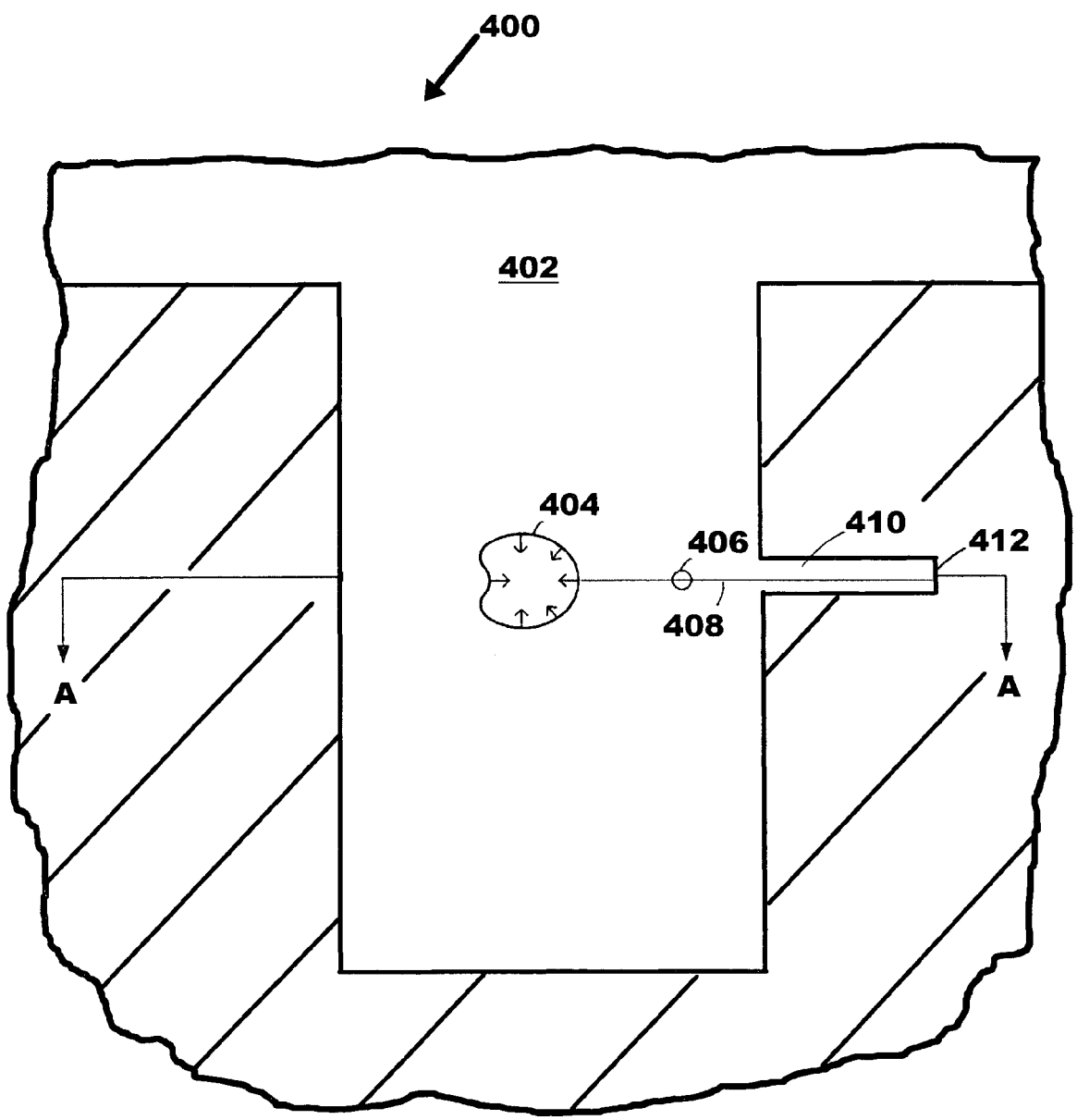
FIG. 9 is a cross sectional view of a cylindrical pore in which the re-entrant micro-jet from a working bubble directed through a target bubble are cutting a cavity in the side wall of the pore in accordance with one embodiment of the present invention.

FIG. 9 is a cross sectional view 400 of a cylindrical pore 420 in which the re-entrant micro-jet 408 from a working cavitation bubble 404 directed through a target bubble 406 are cutting a cavity 410 in the side wall of the pore 402 in accordance with one embodiment of the present invention. Cavitation bubble 404 and target bubble 406 are nucleated within cylindrical pore 402. Re-entrant micro-jet 408 directed toward the wall of pore 402 cuts a channel 410 while impinging on surface 412. The depth of channel 410 will depend on the number of times bubbles 404 and 406 are generated. For pore diameters of 5 to 10 microns, re-entrant micro-jets on the order of 10 to 20 nanometers can be created, creating channels in the side walls in the 20 to 30 nanometer range. In silicon substrates, this could allow fabrication of trench capacitor structures of extremely small dimension, utilizing a volume of the substrate not accessible previously. The fabrication technology may enable true three dimensional device fabrication strategies to produce nanometer device geometry's without the use of lithography.

Figure 10:
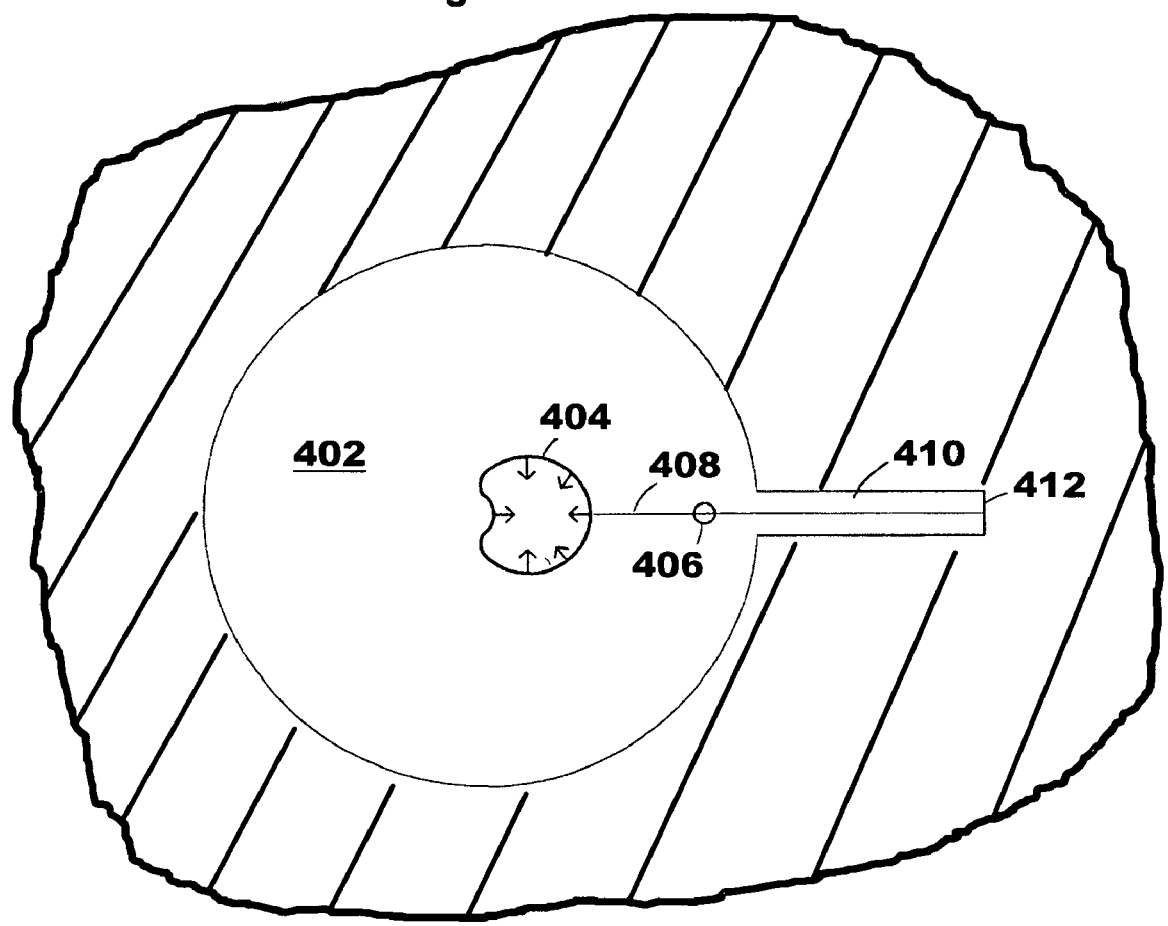
FIG. 10 is a top view looking into the cylindrical pore of FIG. 9 in accordance with one embodiment of the present invention.

FIG. 10 is a top view looking into the cylindrical pore 402 of FIG. 9 in accordance with one embodiment of the present invention.

Figure 11:
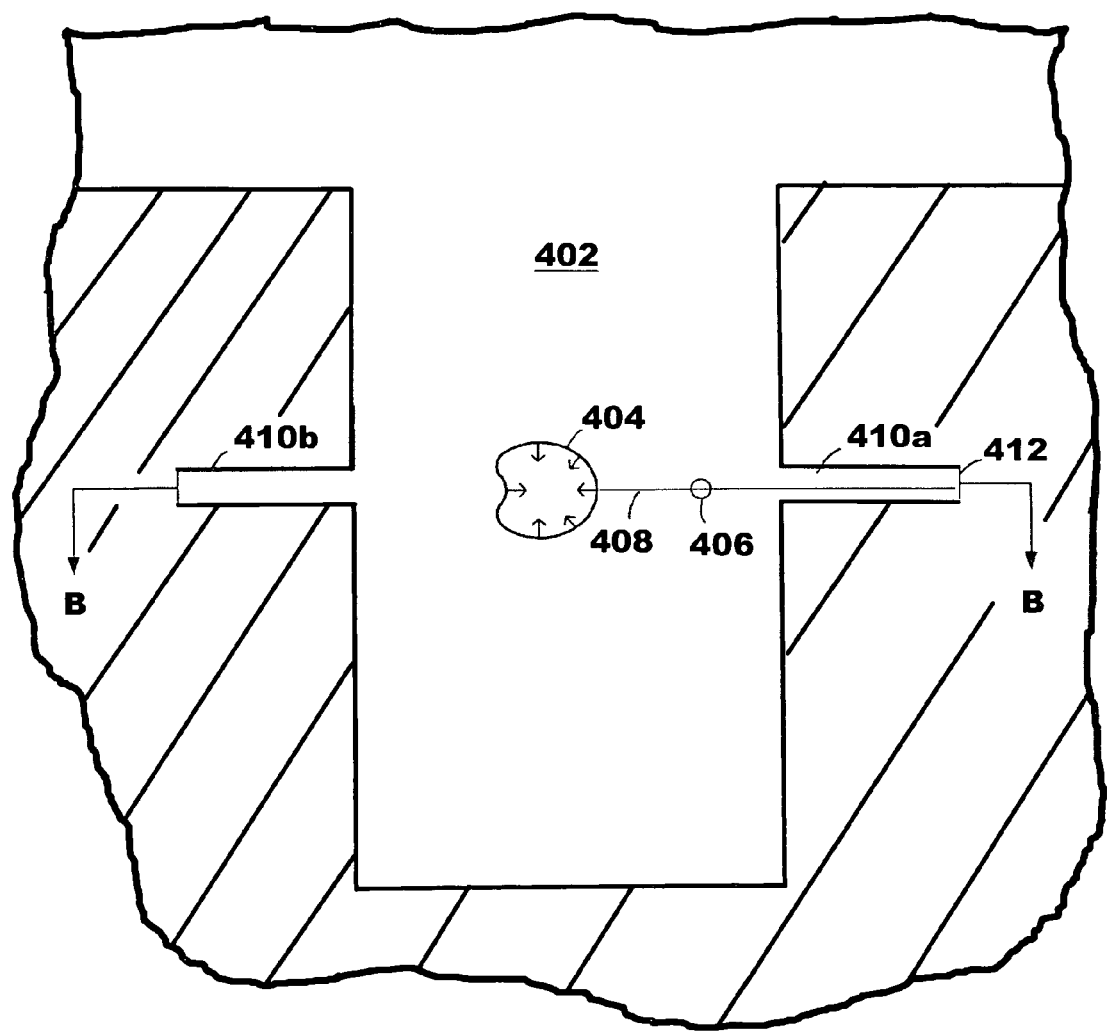
FIG. 11 is a cross sectional view of a cylindrical pore where the re-entrant micro-jets from a working bubble directed through a target bubble are cutting multiple cavities in accordance with one embodiment of the present invention.

FIG. 11 is a cross sectional view of a cylindrical pore where the re-entrant micro-jets from a working bubble directed through a target bubble are cutting multiple cavities in accordance with one embodiment of the present invention. Cavitation bubble 404 is shown cutting multiple cavities 410a and 410b. This can be accomplished by placing target bubble 406 in the appropriate direction.

Figure 12:
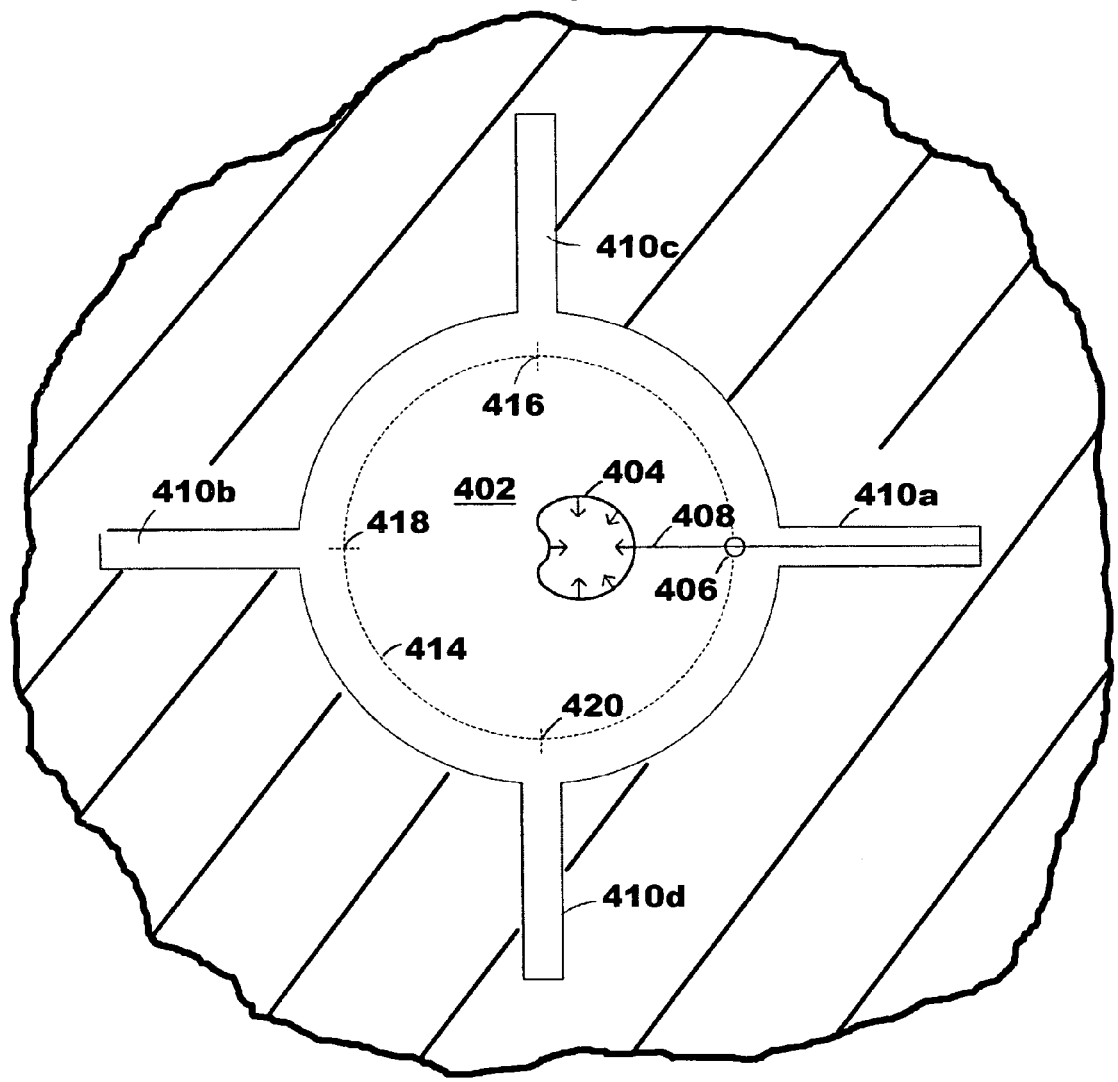
FIG. 12 is a top view looking into the pore of FIG. 11 showing multiple cavities formed at 90 degree angles in accordance with one embodiment of the present invention.

FIG. 12 is a top view looking into the pore of FIG. 11 showing multiple cavities formed at 90 degree angles in accordance with one embodiment of the present invention. By positioning the target bubble 406 on dotted circular path 414 at positions 418, 416, and 420 cavities 410b, 410c, and 410d can be fabricated, respectively. Although four cavities are shown in this figure, many others at any desired spacing can be fabricated as will be appreciated by those skilled in the art.

Figure 13:
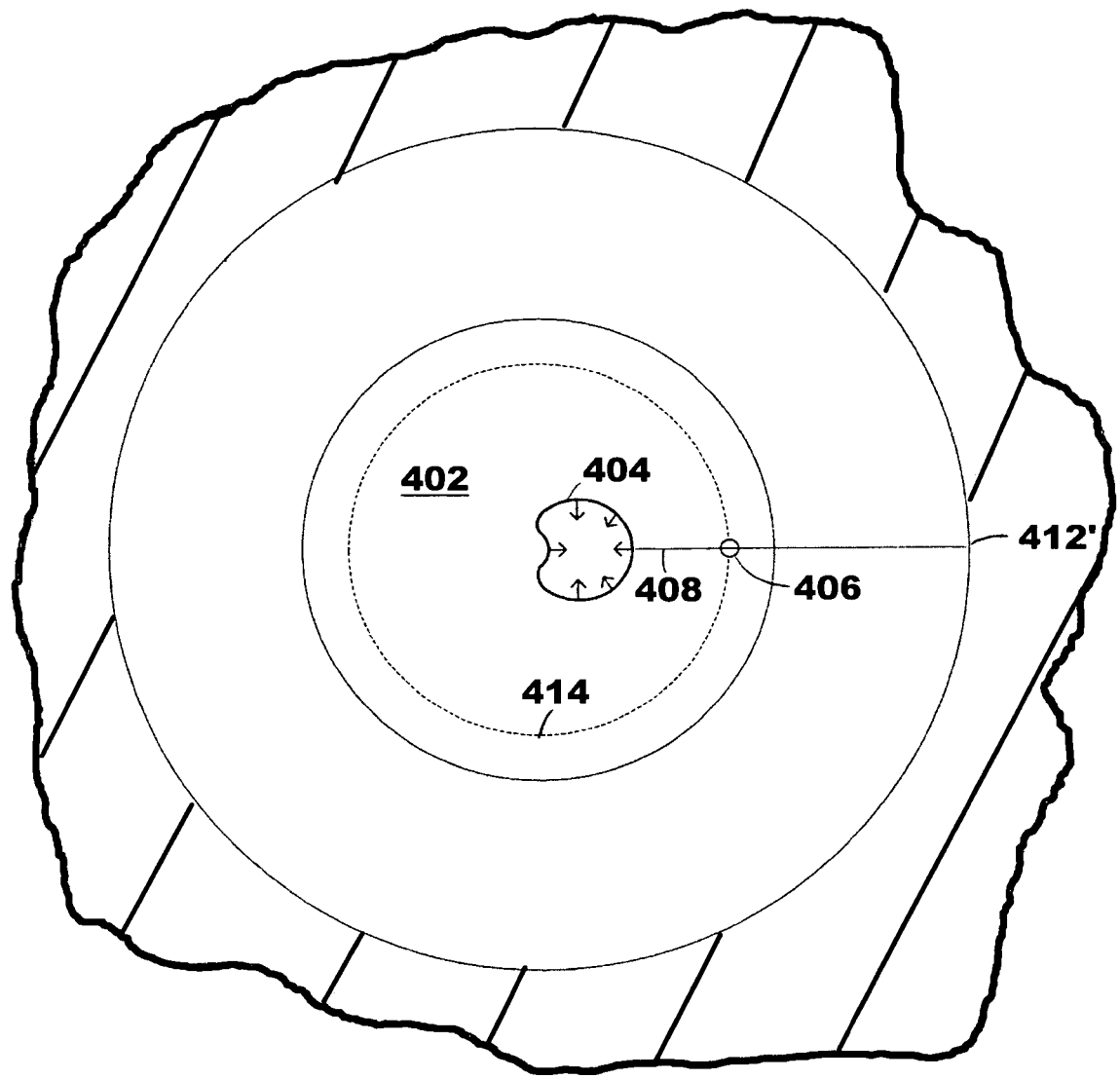
FIG. 13 is a top view looking into the cylindrical pore wherein a continuous slot has been fabricated in accordance with one embodiment of the present invention.

FIG. 13 is a top view looking into the cylindrical pore of FIG. 11 wherein a continuous horizontal slot has been fabricated in accordance with one embodiment of the present invention. When a series of cavitation target bubbles 406 are moved in a continues manner along path 414, a resulting horizontal slot at depth 412' can be produced. By altering the depth that working bubble 404 and target bubble 406 are situated in the pore 402, multiple horizontal slots at varying depths can be fabricated as well. Due to the intense power of the re-entrant micro-jets, the hardest materials can be eroded with this technique, including crystalline silicon. Multiple slots produced in a horizontal fashion could provide a basis for very high surface area capacitors for advanced memory devices.

Figure 14:
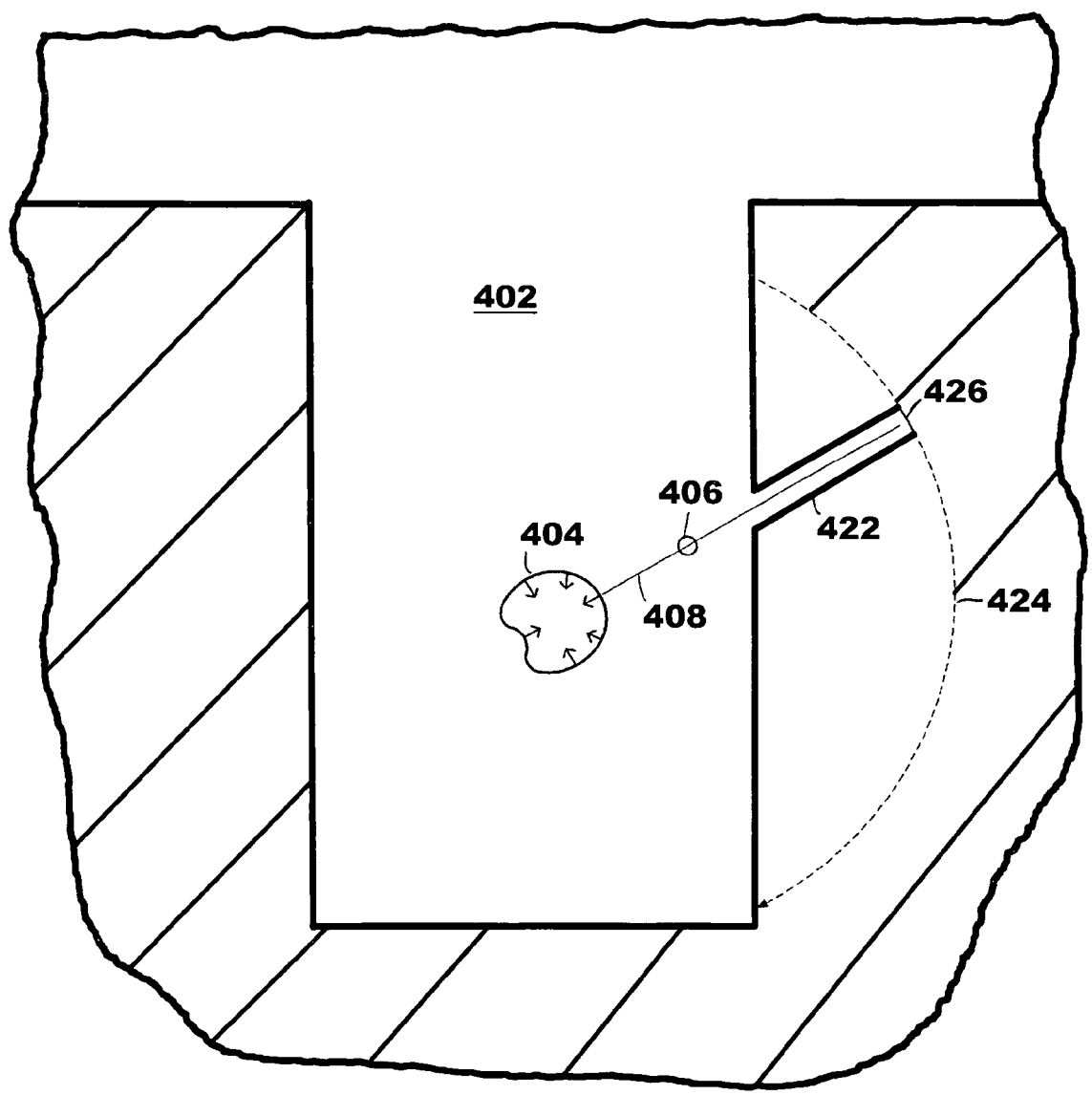
FIG. 14 is a cross sectional view of a cylindrical pore in where the re-entrant micro-jets from a working bubble directed through a target bubble are cutting a cavity at an angle not normal to the surface of the pore in accordance with one embodiment of the present invention.

FIG. 14 is a cross sectional view of a cylindrical pore 402 in where the re-entrant micro-jets 408 from a working bubble 404 directed through a target bubble 406 are cutting a cavity at an angle not normal to the surface of the pore in accordance with one embodiment of the present invention. In this case target bubble 406 is placed in a horizontal plane above or below cavitation bubble 404. If the position of bubbles 404 and 406 are held constant, the re-entrant micro-jet 408 will cut a cavity 422 at an angle to the vertical wall of pore 402. By placing target bubble 406 at fixed depth intervals, cavities at various angles of depth 426 can be produced. By adjusting the depth of target bubble 406 in a continues manner, a larger cutout following the outline 424 may be obtained. By applying the techniques illustrated in the previous FIGS. 9-14, practically any profile or shape can be fabricated in the walls of a pore.

Figure 15:
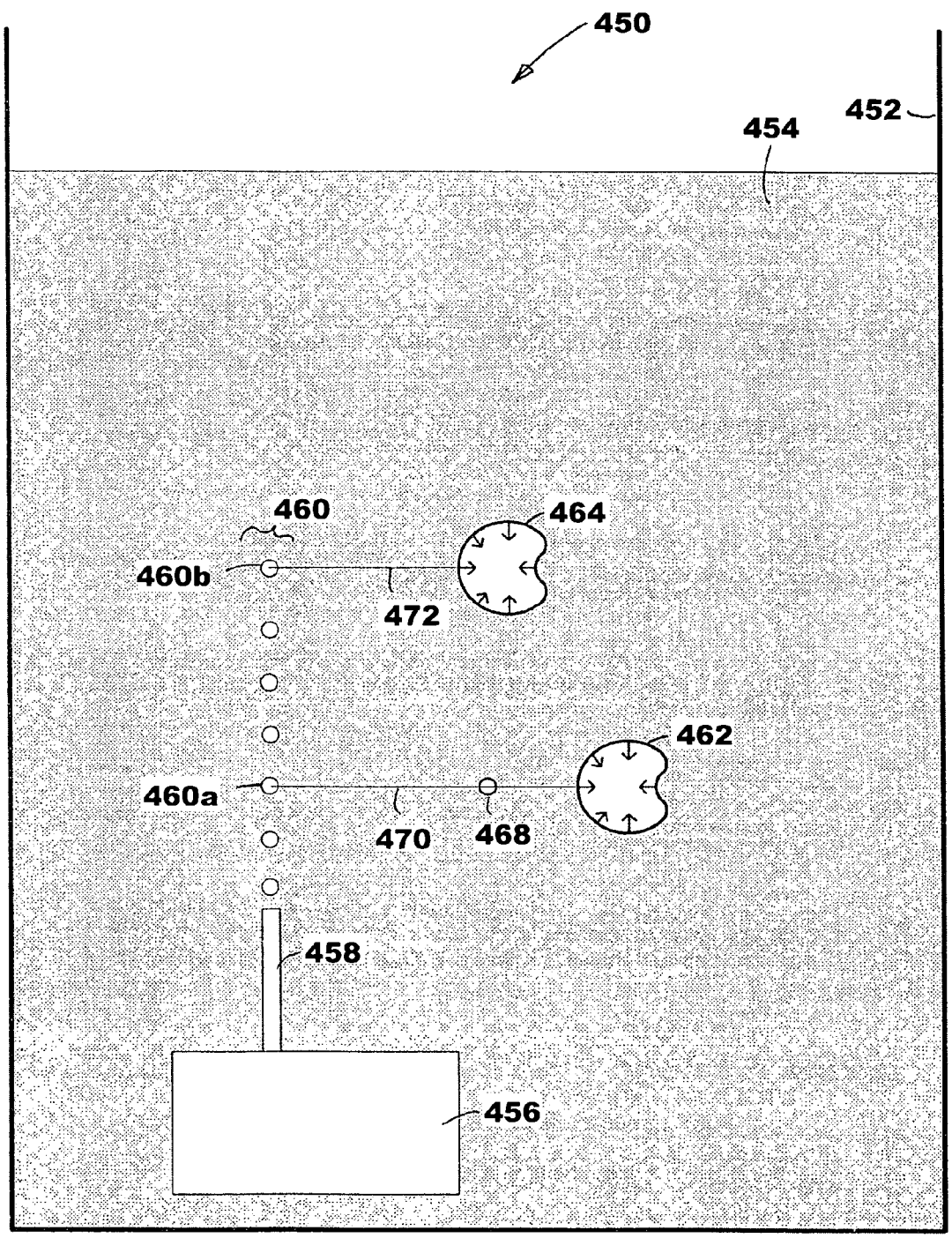
FIG. 15 is a schematic view of a cavitation based process for injecting solution components into lissome in accordance with one embodiment of the present invention.

FIG. 15 is a schematic view of a cavitation based process for injecting solution components into liposomes in accordance with one embodiment of the present invention. Liposomes are microscopic, fluid-filled pouches whose walls are made of layers of phospholipids identical to the phospholipids that make up cell membranes. The fluid inside the pouch may contain soluble drugs designed to be delivered to cells when the liposomes merge with the cell walls of a targeted cell. One way to inject the drug into the interior of a liposome is shown in via the apparatus 450 in this figure. A container 452 contains a fluid solution 454, a liposome manufacturing module 456 (which can also reside outside the walls of container 452), and a nozzle 458 for delivering liposomes 460 to the fluid 454. The liposomes may be manufactured with no drugs in their interiors, some amount of the desired drug, or a mixture of completely different drugs. The drugs to be injected are present in the solution 454. In one example, a cavitation bubble 464 is nucleated within five bubble diameters of a liposome 460b. The liposome acts like a target bubble, attracting the re-entrant micro-jet 472. Adjustment of the control volume and initial energy dose will determine the size of the cavitation bubble, and therefore the size of micro-jet 472. The collapsing cavitation bubble entrains components of the solution 454, including the drugs to be injected, and the micro-jet 472 delivers these components through the wall of the liposome 460b. In a second example, a target bubble 468 is nucleated in the proximity to a working bubble 462, in such a manner as to direct a re-entrant micro-jet 470 into the interior of liposome 460a. This method allows the working bubble 462 to be a further distance from liposome 460a, allowing additional flexibility in reducing dosage levels injected into the liposome, as well as reducing the potentially damaging impact of a jet launched in close proximity.

What is claimed is:

1. A method for the directed formation of a re-entrant micro-jet comprising:
   generating a working cavitation bubble in a liquid, proximate to a work surface; and,
   generating a target bubble in said liquid between said work surface and said working cavitation bubble, wherein a first re-entrant micro-jet formed upon the collapse of said working cavitation bubble is directed to said work surface.

2. The method of claim 1, wherein
   said working cavitation bubble attains a maximum working bubble diameter during expansion;
   said target bubble is within a distance of six said maximum working bubble diameters of the center of said working cavitation bubble.

3. The method of claim 2, wherein said target bubble is greater than 10% of said maximum working bubble diameter prior to the collapse of said working cavitation bubble.

4. The method of claim 3, wherein said target bubble is a cavitation bubble.

5. The method of claim 4, wherein
   said target bubble attains a maximum target bubble diameter during expansion; and
   said target bubble is a distance greater than six said maximum target bubble diameters from a surface of said working bubble.

6. The method of claim 4, wherein
   said target bubble is within six maximum target bubble diameters of said work surface;
   said working bubble is within six maximum working bubble diameters of said work surface; and
   said target bubble launches a second re-entrant micro-jet to said work surface.

7. The method of claim 3, wherein said target bubble is a gas bubble.

8. The method of claim 1, wherein said first re-entrant micro-jet is directed through said target bubble to said work surface.

9. The method of claim 1, wherein said work surface is a portion of a liposome surface.

10. An apparatus for the directed formation of a re-entrant micro-jet comprising:
    a first energy source having an energy flow in a liquid sufficient to create a working cavitation bubble proximate to a work surface; and,
    a second energy source having a second energy flow in said liquid sufficient to create a target cavitation bubble between said work surface and said working cavitation bubble, wherein a first re-entrant micro-jet formed upon the collapse of said working cavitation bubble is directed to said work surface.

11. The apparatus of claim 10 wherein
    said working cavitation bubble attains a maximum working bubble diameter during expansion;

said target bubble is within a distance of six said maximum working bubble diameters of the center of said working cavitation bubble.

12. The apparatus of claim 11, wherein said target bubble is greater than 10% of said maximum working bubble diameter prior to the collapse of said working cavitation bubble.

13. The apparatus of claim 11, wherein
said target bubble attains a maximum target bubble diameter during expansion; and
said target bubble is a distance greater than six said maximum target bubble diameters from a surface of said working bubble.

14. The apparatus of claim 10, wherein said first re-entrant micro-jet is directed through said target bubble to said work surface.

15. The apparatus of claim 10, wherein said first energy source is a laser.

16. The apparatus of claim 10, wherein said first energy source is an x-ray source.

17. The apparatus of claim 10, wherein said first energy source is an electrical discharge device.

18. The apparatus of claim 10, wherein said second energy source is a laser.

19. The apparatus of claim 18, wherein said laser includes one of an excimer, dye, Nd-YAG, or CO2 laser.

20. The apparatus of claim 10, wherein said second energy source is an x-ray source.

21. The apparatus of claim 15, wherein said laser includes one of an excimer, dye, Nd-YAG, or CO2 laser.

* * * * *